United States Patent [19]
Dahl et al.

[11] Patent Number: 5,268,289
[45] Date of Patent: Dec. 7, 1993

[54] THERMOSTABLE RIBONUCLEASE H

[75] Inventors: Gary A. Dahl; Jerome J. Jendrisak, both of Madison, Wis.

[73] Assignee: Epicentre Technologies Corp., Madison, Wis.

[21] Appl. No.: 815,095

[22] Filed: Dec. 27, 1991

[51] Int. Cl.[5] .................. C12N 9/00; C12N 9/22; C12N 9/14; C12N 9/16
[52] U.S. Cl. ................... 435/199; 435/183; 435/195; 435/196
[58] Field of Search ............ 435/199, 183, 195, 196

[56] References Cited

U.S. PATENT DOCUMENTS

| | | | |
|---|---|---|---|
| 3,896,000 | 7/1975 | Kamekura et al. | 435/199 |
| 4,889,818 | 12/1989 | Gelford et al. | 435/194 |

FOREIGN PATENT DOCUMENTS

| | | | |
|---|---|---|---|
| 2-057181 | 2/1990 | Japan | 435/199 |
| 1495377 | 7/1989 | U.S.S.R. | 435/199 |

OTHER PUBLICATIONS

Duck, P. et al., "Probe Amplifier System Based on Chimeric Cycling Oligonucleotides," Biotechniques, 9[2]: 142 (1990).
Itaya et al. Nucleic Acids Research, 19(16), 1991, 4443-4450.
Crouch, R., in Gene Amplification and Analysis (1981) (Cherikjian, J. G., and Popas, T. S., eds.) 2: 217-228, Elsewier, North Holland, N.Y.
Okayama, H., et al. "High-Efficiency Cloning of Full-Length cDNA," Mol. Cell. Biol. 2[2]: 161-170 (1982).
Jendrisak, J. "The use of Polyethyleneimine in Protein Purification," Protein Purification: Micro to Macro, pp. 75-97 (1987).
Lawyer, F. C. et al., "Isolation, Characterization, and Expression in Escherichia coli of the DNA Polymerase Gene from Thermus aquaticus," J. Biol. Chem., 264 [11]: 6427-6437 (1989).
Guatelli, J. C., et al. "Isothermal, in vitro amplication of nucleic acids by a multienzyme reaction modeled after retroviral replication," Proc. Natl. Acad. Sci. USA, 87: 1874-1878 (1990).
Kuze, et al., "A new vector and RNase H method for the subtractive hybridization," Nucleic Acids Res., 17[2]: 807 (1989).
Minshull, J., et al., "The use of single-stranded DNA and RNase H to promote quantitative 'hybrid arrest of translation' of mRNA/DNA hybrids in reticulocyte lysate cell-free translations," Nucleic Acids Res., 14[16]: 6433-6451 (1986).
Krug, M. S. et al., "Determination of the Molar Concentration of Messenger RNA," Methods in Enzymology, 152: 262-317 (1987).
Crouch, R. et al. "Ribonucleases H" in Nuclease (1982) (Levin, S. M., and Roberts, R. J. eds) pp. 211-241, Cold Spring Harbor Laboratory, Cold Spring Harbor, N.Y.
Kanaya, S. et al. "DNA Sequence of the Gene Coding for Eschericha coli Ribonuclease H," J. Biol. Chem., 258[2]: 1276-1281 (1983).
Berkower, I., et al., "Isolation and Characterization of an Endonuclease from Escherichia coli Specific for Ribonucleic Acid in Ribonucleic Acid Deoxyribonucleic Acid Hybrid Structures," J. Biol. Chem., 248[17]: 5914-5921 (1973).
Gubler U., et al., "A simple and very efficient method for generating cDNA libraries," Gene, 25: 263-269 (1983).

Primary Examiner—Douglas W. Robinson
Assistant Examiner—L. Blaine Lankford
Attorney, Agent, or Firm—Quarles & Brady

[57] ABSTRACT

A substantially pure preparation of thermostable RNase H is disclosed. In one preferable form of the invention, the RNase H is capable of biological activity after incubation at temperatures equal to or greater than 70° C. for at least ten minutes. In another preferable form of the invention, the purification is from Thermus thermophilus or a closely related organism. The present invention is also a method of digesting RNA polymers that are in duplex form with a DNA molecule. The method comprises exposing the duplex to the isolated thermostable RNase H.

3 Claims, 4 Drawing Sheets

THERMOSTABLE RIBONUCLEASE H

FIELD OF THE INVENTION

The present invention relates to the field of molecular biology. More specifically, the present invention relates to the creation and use of the novel enzyme, thermostable ribonuclease H.

BACKGROUND OF THE INVENTION

Ribonuclease H (endoribonuclease H, EC 5.1.26.4, hereafter referred to as RNase H) is an enzyme capable of hydrolyzing an RNA molecule when the RNA molecule is hybridized with a complementary DNA strand. The biological role of the enzyme is not known, and hence it is not known whether all organisms possess this enzyme.

RNase H is a useful tool in molecular biology research. RNase H is used for degrading the RNA strand after first-strand synthesis in the production of double-stranded cDNA. Okayama, H., et al. (1982) Mol. Cell. Biol. 2: 161-170.6; Gubler, U., et al. (1983) Gene 25: 263-269. The enzyme can remove poly-(A) tails from messenger RNA if the mRNA is reacted with oligo-dT$_{12-18}$. Vournakis, J., et al. (1975) Proc. Natl. Acad. Sci. USA 72: 2959-2963; Davis, R., et al. (1988) Mol. Cell. Biol. 8: 4745-4755.

Most importantly, RNase H is used as a diagnostic tool for detecting specific target DNA sequences in a biological sample by a probe amplification process. Duck, P., et al. (1990) BioTechniques 9: 142-147. In this diagnostic technique, a probe is made of ribonucleoside bases flanked by deoxy-ribonucleoside bases. The probe hybridizes to a target DNA molecule. RNase H digests the ribonucleoside bases and cleaves the probe. The probe fragments then dissociate from the target. After many cycles, these fragments accumulate and serve as a basis for detecting the presence of the target.

RNase H is a component of another diagnostic test called the self-sustained sequence replication (3SR) amplification system, which is a transcription-based amplification method. Guatelli, J. C., et al. (1990) Proc. Natl. Acad. Sci. USA 87: 1874-1878. In the 3SR system, a target nucleic acid sequence is replicated exponentially by using RNase H, a DNA-dependent RNA polymerase and reverse transcriptase.

RNase H may also be used to map the location of sequences on an RNA molecule. First the RNA is annealed with specific oligodeoxyribonucleotide probes and then the duplexed RNA is cleaved with RNase H. Donis-Keller, H. (1979) Nucleic Acids Res. 7: 179-192.

RNase H may also be used to quantitate poly-(A)-containing mRNA in biological samples. Krug, M. S., et al. (1987) Methods Enzymol. 152: 262-266. RNase H is useful in cDNA cloning via subtractive hybridization (Kzze, K., Shimizu, et al. (1989) Nucleic Acids Res. 17: 807) and for hybrid-arrest translation (Minshull, J., et al (1986) Nucleic Acids Res. 14: 6433-6451).

The RNase H enzyme used in the above-mentioned research was isolated from *E. coli*. The *E. coli* enzyme is called "RNase HI" and is the product of the rnhA gene. Berkower, I., et al. (1973) J. Biol. Chem. 248: 5914-5921; Kanaya, S., et al. (1983) J. Biol. Chem. 258: 1276-1281. RNase H has been identified in other organisms besides *E. coli*, such as yeast, KB cells, Krebs II ascites cells and avian myeloblastosis virus infected cells, although its existence in other species is still unknown. Crouch, R. J. (1981) in *Gene Amplification and Analysis* (Chirikjian, J. G., and Papas, T. S., eds.) Vol. 2, pp. 218-228, Elseivier, North Holland, N.Y.; Crouch, R. J., et al. (1982) in Nuclease (Linn, S. M., and Roberts, R. J., eds.) pp. 211-241, Cold Spring Harbor Laboratory, Cold Spring Harbor, N.Y. No RNase H has been isolated from any thermophilic organisms.

A thermostable RNase H would be preferable in many RNase H applications, particularly for mapping and certain diagnostic applications. In addition to the obvious advantages of longer reagent shelf life and greater stability under reaction conditions, a thermostable RNase H would allow reactions to be carried out at higher temperatures. These higher temperatures are closer to optimal temperatures for hybridization of RNA probes to target DNA and would destroy the activity of *E. coli* RNase H. The optimum temperature for a nucleic acid hybridization will depend on the hybridization buffer, but typically reaction temperatures in the 70° C. to 95° C. range facilitate maximum sensitivity by ensuring that target DNA sequences are melted and accessible and reaction temperatures in the 45° C. to 75° C. range facilitate maximum selectivity of hybrid formation because there is more hybridization stringency at higher temperature. High stringency conditions result in lower background by minimizing non-specific binding of probes to unrelated target sequences.

What is needed in the art of molecular biology is an isolated RNase H capable of biological activity at elevated temperatures. Such an RNase H should be capable of biological activity after incubation at temperatures greater than 45° C. for at least ten minutes. Preferably the RNase H will be capable of biological activity after incubation at temperatures of at least 70° C. for at least ten minutes.

SUMMARY OF THE INVENTION

The present invention is a substantially pure preparation of thermostable RNase H. In one preferable form of the invention, the RNase H is capable of biological activity after incubation at temperatures of at least 70° C. for at least ten minutes. In another preferable form of the invention, the purification is from *Thermus thermophilus* HB8 or a related organism.

The present invention is also a method of digesting RNA polymers that are in duplex form with a DNA molecule. By "DNA" and "RNA" we mean naturally occurring DNA and RNA and chemically and enzymatically modified DNA and RNA. We also mean to include DNA and RNA that is synthetically made and DNA and RNA that contains variant bases. The method comprises exposing the duplex to the isolated thermostable RNase H. In a preferable form of the invention, the DNA molecule is not digested by the RNase H.

It is an object of the present invention to provide a RNase H capable of activity at incubation temperatures close to the optimal temperatures for hybridization of RNA probes to target DNA.

It is another object of the present invention to provide an RNase H capable of activity after incubation at temperatures greater than 45° C. for at least ten minutes.

It is another object of the present invention to provide an RNase H capable of activity after incubation at temperatures of at least 70° C. for at least ten minutes.

It is another object of the present invention to provide a method for digesting an RNA molecule when the RNA molecule is hybridized to a DNA molecule.

It is another advantage of the present invention that the RNase H will not become inactivated when incubated at a temperature of greater than 45° C.

It is another advantage of the present invention that the method of digesting RNA can take place at higher temperatures.

Other objects, advantages and features of the present invention will become apparent from the following specification taken in conjunction with the accompanying drawings.

DETAILED DESCRIPTION OF THE INVENTION

1. In General

Figure 1:
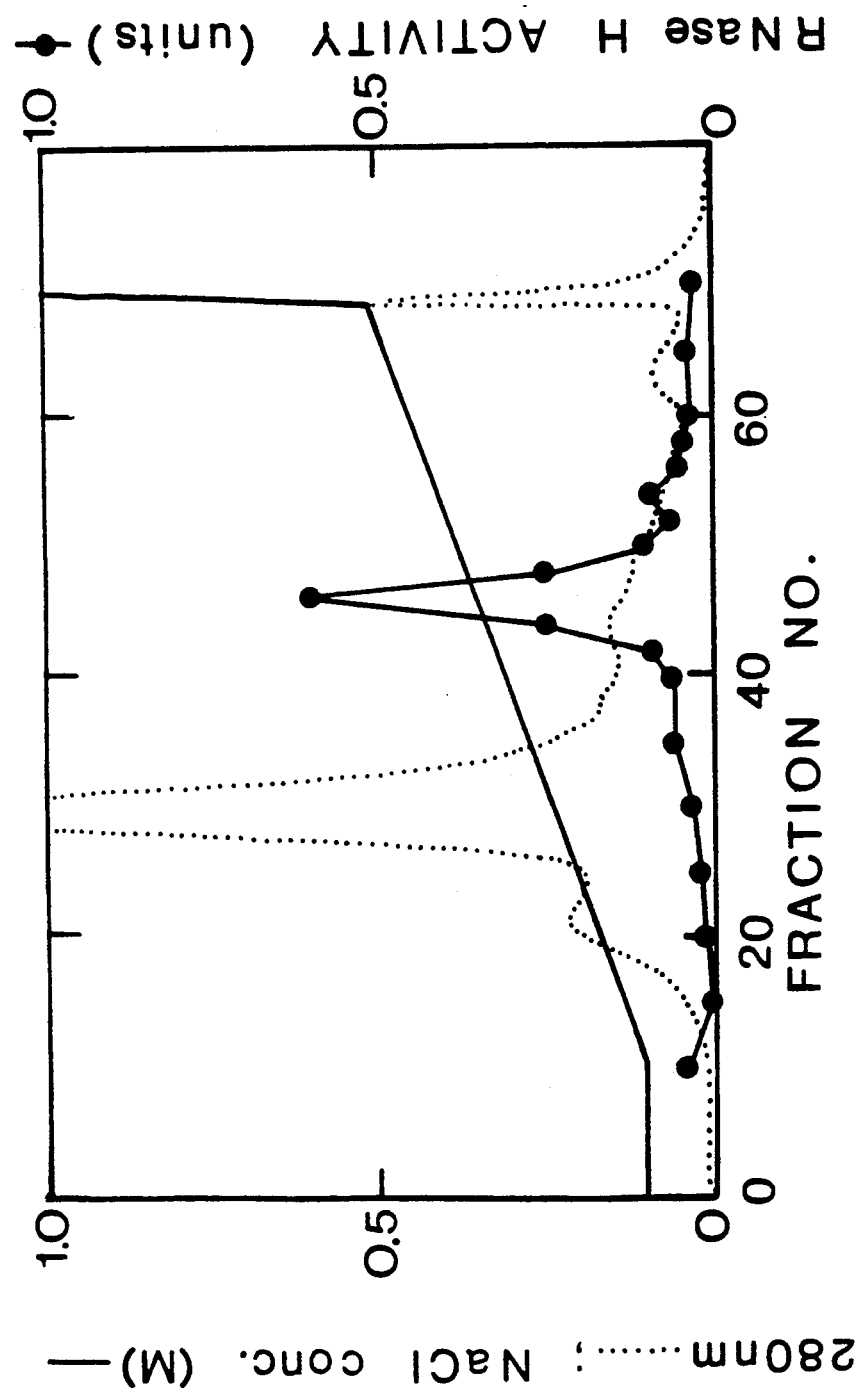
FIG. 1 is a chromatogram of *T. thermophilus* RNase H on BioRex 70.

The present invention requires a substantially pure preparation of a thermostable RNase H. By "substantially pure" we mean a preparation capable of digesting an RNA molecule when the RNA molecule is hybridized to a DNA molecule. The present invention is also a preparation of RNase H of greater than 0.01 Units/$\mu$g (units are defined below). Preferably, the preparation is greater than 1 Units/$\mu$g. This preparation should not contain substantial amounts of other enzymes or constituents that would be detrimental to the RNase H function. By "thermostable" we mean the enzyme will have not lost significant biological activity after incubation over 45° C. for ten minutes. Preferably the enzyme will have significant and useful biological activity after being incubated at temperatures greater than 70° C. for ten minutes. The existence of thermostable RNase H was previously unknown. Here, we have successfully purified a thermostable RNase H, thereby proving the existence of such an enzyme, and also described a methodology for isolation other species of RNase H from other thermophilic organisms.

2. Purification of RNase H from a Thermostable Organism

In order to obtain thermostable RNase H from its native host, an appropriate thermostable microorganism must be identified and cultured. Suitable microorganisms are those which contain a thermostable RNase H capable of isolation and biological activity. *Thermus thermophilus* HB8, *Thermus aquaticus* YT-1, *Thermus flavus*, and *Bacillus stereothermophilus* were discussed in the examples below, but other microorganisms are equally suitable. Organisms that are closely related to *Thermus thermophilus* HB8, such as *Thermus thermophilus* HB27, are particularly suitable. Standard fermentation methods are used to obtain a sufficient amount of the microorganism to isolate the RNase H.

Additionally, the RNase H gene may be cloned from an appropriate source, such as *Thermus thermophilus* HB8, and expressed in a non-thermostable host, such as *E. coli*. Suitable quantities of the enzyme can then be produced by the heterologous host and the enzyme recovered by conventional means for recovering protein produced in such a host. A non-thermostable RNase H may be cloned and then selectively mutagenized to acquire a thermostable enzymatic activity. This could effectively be done by creating oligonucleotide sequences coding for the portions of the thermostable RNase H different from the *E. coli* enzyme and replacing those sequences in the *E. coli* RNase H gene.

The RNase H enzyme can also be isolated from other thermophilic microorganisms in an analogous procedure to the one detailed below. A first consideration is an assay for the presence of the enzyme in different purification fractions. Typically, this is done by examining a fraction for the presence of RNase H activity and a protein of the appropriate size.

The RNase digesting ability of RNase H may be detected in many ways. In the examples below, we disclose a suitable method of testing for RNase H activity. RNase H activity is assayed in a 100 $\mu$l reaction mixture containing: 1 mM poly-(rA); 100 $\mu$M oligo-(dT)$_{18}$; 0.01M Tris-HCl, pH 7.5; 10 mM MgCl$_2$, 0.1 mM EDTA; 1 mM dithiothreitol; 0.1M NaCl; and the purification fraction. The poly-(rA) and oligo-(dT) molecules will form duplexes. If RNase H is present, the poly-(rA) in the duplex will be digested and the oligo-(dT) will be free to from another duplex. Thus, the reaction will "cycle". The digested ribonucleosides are acid soluble and may be spectrophotometrically monitored. After incubation at 45° C. for 20 minutes, 1 ml of ice-cold 5% trichloroacetic acid is added to the reaction mixture. After incubation on ice for 5 minutes, the precipitate is removed by microcentrifuge centrifugation. The absorbance of the supernatant solution is determined at 260 nm in a spectrophotometer. One unit of RNase H is defined here as the amount of enzyme generating 1 nmole of acid-soluble product in 20 minutes under the above conditions.

Preferably, during the purification all initial steps are conducted at 4° C. The chromatographic steps are conducted at room temperature. Purification of RNase H is preferably monitored by sodium dodecyl sulfate polyacrylamide gel electrophoresis (SDS-PAGE). The stained electrophoretic gels are monitored for the occurrence of a protein of the appropriate size. *Thermus thermophilus* RNase H is approximately 20,000 d. RNases H isolated from other organisms are of comparable size. For instance, *E. coli* RNase H is approximately 17,500 d.

Preferably, 1 Kg of cells is suspended in a buffer containing 50 mM Tris-HCl, pH 7.5; 1.0 mM EDTA; 0.1% (v/v) 2-mercaptoethanol; and 5% (v/v) glycerol (abbreviated as TEBG buffer). The cells are lysed and the lysate is treated with polyethyleneimine to precipitate the nucleic acids. The lysate is centrifuged. The pellet contains nucleic acids and is discarded.

At this point, it is useful to subject the supernatant to ammonium sulfate precipitation. The protein fraction that precipitates between 33% and 45% saturation with ammonium sulfate contains RNase H. This precipitate is collected by centrifugation, dialyzed against TEBG buffer and then dialyzed against TEBG buffer additionally containing 0.05M NaCl for approximately 6 hours or until the sample is the same conductivity as the BioRex 70 chromatography buffer.

After dialysis, the solution is preferably applied to a BioRex 70 column equilibrated with TEBG/0.05M NaCl buffer. The purpose of the BioRex 70 column is to remove contaminating proteins.

The unbound protein is washed from the Bio Rex 70 column with the TEBG/0.05M NaCl buffer. RNase H is eluted from the column with a salt gradient of 0.05–0.5M NaCl. In the example below, a single activity peak was eluted at approximately 0.3M NaCl, but the elution point might vary from preparation to preparation. The fraction containing RNase H activity may be located by either an RNase H assay or SDS-PAGE analysis.

Fractions containing RNase H are pooled and the protein is precipitated with ammonium sulfate at 66% saturation. This precipitate is collected by centrifugation and dissolved in a small volume of TEBG buffer.

The dissolved sample is then preferably chromatographed on a Sephacryl S-100 HR sizing column. The purpose of this column procedure is to separate the proteins contained in the sample by size. Fractions are taken from this column and each fraction analyzed for RNase H activity. Protein concentration in the column fractions may be determined by a protein assay, such as the Bradford assay. Bradford, M. M. (1976) *Anal. Biochem.* 72: 248–254. Fractions containing RNase H are pooled and dialyzed against TEBG/0.05 NaCl.

This pooled sample is preferably chromatographed on a heparin agarose column equilibrated with TEBG/0.05 NaCl buffer. The heparin agarose column procedure removes additional protein contaminants. Fractions are assayed for RNase H activity and aliquots are electrophoresed on SDS-PAGE. Fractions containing RNase H are pooled and dialyzed against storage buffer. The enzyme may then be stored at −20° C. A typical storage buffer is 0.05M Tris-HCl, pH 7.5; 0.1 mM EDTA; 1 mM dithiothreitol; 0.1M NaCl, 50% (v/v) glycerol; and 0.1% (v/v) Triton X-100.

3. Thermostability Analysis

A newly isolated RNase H must be analyzed for thermostability to verify the desired level of that trait. This is most easily done in a comparison test with *E. coli* RNase H, as described below in the Examples. Basically, the new RNase H and *E. coli* RNase H are individually preincubated in a reaction buffer without poly-(rA) and oligo-(dT). RNase H activity is determined after adding poly-(rA) and oligo-(dT). The reaction mixture is incubated at different temperatures to determine the temperature stability range of the RNase H. In the examples below, the RNase H digestions were incubated for ten minutes at 37° C., 45° C., 70° C. and 90° C. in 50 μl of reaction buffer containing 0.01M Tris-HCl, pH 7.5, 10 mM MgCl$_2$, 0.1 mM EDTA, 1 mM dithiothreitol, and 0.1M NaCl.

After readjusting the incubation temperature back to 20° C., poly-(rA) and oligo-(dT) are added to the enzyme-containing solution and the RNase H activity determined. An RNase H is "thermostable" if after incubation at temperatures greater than 45° C. for ten minutes, the RNase H is capable of digesting the added poly-(rA). In the example below, the RNase H from *Thermus thermophilus* was incubated at 45° C. to obtain optimum digestion, as compared to 37° C. for *E. coli* RNase H.

4. Purity of Enzyme

A single unit of RNase H activity was defined above as the amount of enzyme generating 1 nmole of acid-soluble product in 20 minutes in the assay for RNase H activity described above. By using the purification protocol generally described above, it is possible to reliably isolate thermostable RNase H in a purity such that the activity level is above 100 units μg total protein. Since as produced in its native organism, the concentration of thermostable RNase H is less than 0.01 units per μg, this represents a concentration of the enzyme in excess of 10,000 times over its concentration in the native organism. In general, separated functions recovered from host organisms which have activity levels in excess of 0.1–1 units per μg total protein would provide useful levels of enzyme concentrations for at least some molecular biology procedures. At a purification of 10 units per μg, still ten-fold less than is possible by our purification method, the preparation is useful for many more molecular biology procedures.

EXAMPLES

1. Purification of RNase H from Thermus thermophilus.

*Thermus thermophilus* HB8 strain (available without restriction from the American Type Culture Collection, 12301 Parklawn Drive, Rockville, Md. as ATCC No. 27634) was grown in a 300 liter fermenter in the following medium: 4 g/L yeast extract; 8 g/L peptone; and 2 g/L NaCl. The pH was controlled at 7.5–8.0 with ammonium hydroxide, the dissolved oxygen was maintained at 40%, the temperature was maintained at 70° C., and the stirring rate was maintained at 400 rpm. Cells were harvested by centrifugation at late log phase at a cell density of approximately 5 g/L.

RNase H activity was assayed in a 100 μl reaction mixture containing: 1 mM poly-(rA); 100 μM oligo(dT)$_{18}$; 0.01M Tris-HCl, pH 7.5; 10 mM MgCl$_2$, 0.1 mM EDTA; 1 mM dithiothreitol; 0.1M NaCl and the purification fraction. After incubation at 45° C. for 20 minutes, 1 ml of ice-cold 5% trichloroacetic acid was added to the reaction mixture. After incubation on ice for 5 minutes, the precipitate was removed by microcentrifuge centrifugation. The absorbance of the supernatant solution was determined at 260 nm in a spectrophotometer. One unit of RNase H was defined as the amount of enzyme generating 1 nmole of acid soluble product in 20 minutes under the above conditions.

Purification of RNase H was monitored by tris-glycine, sodium dodecyl sulfate polyacrylamide gel electrophoresis (abbreviated as SDS-PAGE). The gels contained 15% acrylamide with an acrylamide/bis-acrylamide ratio of 30:1. Gels were electrophoresed, stained in Coomassie brilliant blue, and destained by standard methods, Laemmli, U. K. (1970) *Nature* 277: 680–685. A set of polypeptides (described below) was used as a molecular weight standard.

*T. thermophilus* RNase H was purified using the following protocol. All of the purification steps were conducted at 4° C. with the exception of the chromatographic steps, which were conducted at room temperature. 1 kg of cells was suspended in a buffer consisting of 50 mM Tris-HCl, pH 7.5; 1.0 mM EDTA; 0.1% (v/v) 2-mercaptoethanol; and 5% (v/v) glycerol (abbreviated as TEBG buffer). Cells were lysed and the lysate was treated with polyethyleneimine to precipitate the nucleic acids. Jendrisak, J. (1987) in *Protein Purification* (Burgess, R. R., ed.), Alan R. Liss, Inc., New York, N.Y., pp. 75–97.

After centrifugation, the protein fraction precipitating between 33% and 45% saturation with ammonium sulfate was collected by centrifugation and was dissolved against TEBG buffer. The resulting solution was dialyzed against TEBG buffer containing 0.05M NaCl.

The dialysate was applied to a 2.5-cm×15-cm column of BioRex 70 equilibrated with TEBG buffer containing 0.05M NaCl. After washing unbound protein from the column with the same buffer, RNase H was eluted from the column with 10 column volumes of a salt gradient of 0.05–0.50M NaCl. Fractions of approximately 20 ml were collected.

A single activity peak was eluted at approximately 0.30M NaCl from the column. The protein was continuously monitored at 280 nm with an Isco Model UA-5 absorbance monitor. FIG. 1 is a chromatogram showing the RNase H peak. Flowthrough and wash fractions are not shown on the FIG. 1 chromatogram. 50 μl aliquots were assayed for RNase H activity. Fractions 43–49 were pooled and protein concentrated for subsequent chromatography on Sephacryl S-100 HR. 5 μl aliquots of every fifth column fraction were subjected to an SDS-PAGE analysis along with a lane of polypeptide molecular weight markers. Fractions 45–50 had a protein band at approximately 20 Kd, suggesting that RNase H was present.

The active fractions (43–49) were pooled and the protein was precipitated with ammonium sulfate at 66% saturation. The precipitate was collected by centrifugation and was dissolved in a small volume of TEBG buffer. The protein sample was then chromatographed on a 2.5-cm×122-cm Sephacryl S-100 HR sizing column equilibrated with TEBG/0.5M NaCl. Fractions of approximately 20 ml were collected. A single peak of RNase H activity eluted at approximately 1.6 times the void volume of the column.

Figure 2:
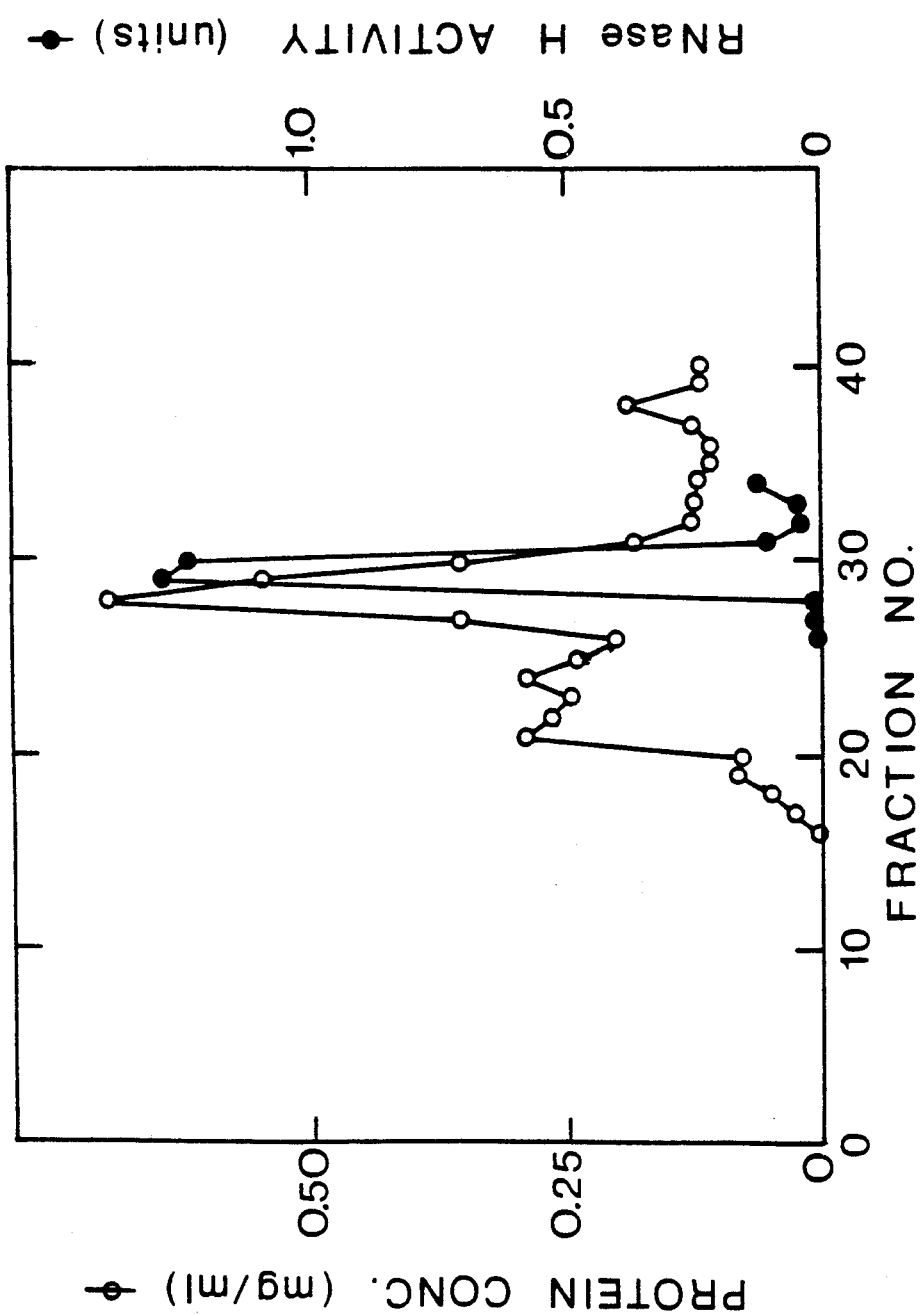
FIG. 2 is a chromatogram of *T. thermophilus* RNase H on Sephacryl 5100 HR.

FIG. 2 is a chromatogram showing the RNase H peak. The protein concentration in the column fractions was determined by the Bradford dye-binding assay, Bradford, M. M. (1976) Anal. Biochem. 72: 248–254, and the RNase H activity was determined with 10 μl aliquots of column fractions. RNase H activity was detected in fractions 29 and 30. These fractions were pooled for dialysis. An SDS-PAGE analysis was performed on 5 μl aliquots of fractions. Fraction 29 and 30 showed a band at 20 Kd.

Figure 3:
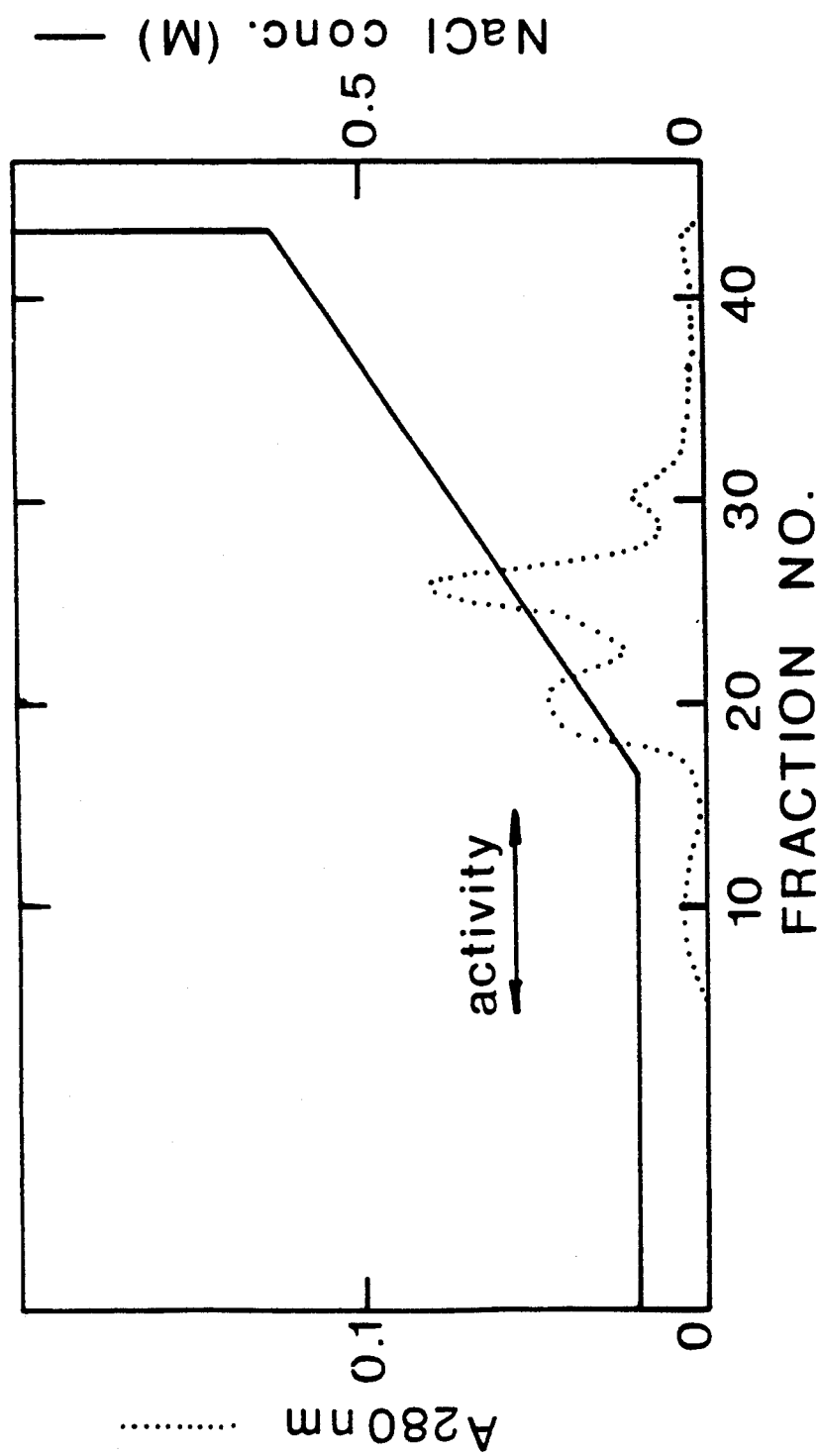
FIG. 3 is a chromatogram of *T. thermophilus* RNase H on heparin agarose.

The pooled fractions were dialyzed against TEBG buffer containing 0.05M NaCl. The sample was chromatographed on a 1.5-cm×10-cm heparin agarose column equilibrated with TEBG buffer containing 0.05M NaCl. FIG. 3 is a chromatogram that shows the results of this procedure. RNase H was eluted from the column with the same buffer and contaminants were eluted with 10 column volumes of a salt gradient of 0.05–0.25M NaCl. Fractions of approximately 4 ml were collected.

Still referring to FIG. 3, protein was continuously monitored at 280 nm with an Isco Model UA-5 absorbance monitor and RNase H activity was determined with 10 μl aliquots of column fractions as described above. Additionally, an SDS-PAGE analysis was performed on 5 μl aliquots of the heparin agarose column fractions. Fractions 8–16 contained a single polypeptide band of molecular weight 20,000 d. These fractions exactly correlated with RNase H activity in the column fractions. Fractions 7–16 were pooled and dialyzed against storage buffer prior to storage of enzyme at −20° C. The fractions were dialyzed for 16 hours at 4° C. against a storage buffer containing 0.05M Tris-HCl, pH 7.5; 0.1 mM EDTA; 1 mM dithiothreitol; 0.1M NaCl, 50% (v/v) glycerol; and 0.1% (v/v) Triton X-100.

2. Characterization of the Purified Enzyme

The molecular weight of T. thermophilus RNase H was determined by SDS-PAGE. One μg of the protein and each marker was subjected to analysis. Marker proteins were phosphorylase b (94,000), bovine serum albumin (67,000), ovalbumin (43,000), carbonic anhydrase (30,000), soybean trypsin inhibitor (20,100), and lactalbumin (14,400). The data from the SDS-PAGE indicated that T. thermophilus RNase H has a molecular weight of about 20,000. This is similar to the molecular weight of E. coli RNase HI. E. coli RNase HI has a published molecular weight of 17,559 based on the derived amino acid sequence. Kanaya, S. et al. (1983) J. Biol. Chem. 258: 1276–1281.

Amino acid analysis of the isolated RNase was performed on an Applied Biosystems 420-A-03 micro amino acid analyzer/derivatizer. Cysteine residues were first pyridylethylated after the protein was fully denatured and any disulfides reduced. The amino acid composition of Thermus thermophilus RNase H is presented and compared to the composition of E. coli RNase H in Table 1. The composition of the E. coli enzyme was derived from the DNA sequence of the rnh A gene. Kanaya, S. et al. (1983) J. Biol. Chem. 258: 1276–1281. Amino acid composition indicates that the molecular weight of Thermus thermophilus RNase H is 20,018, which is in good agreement with the value derived from SDS-PAGE.

N-terminal microsequencing was done on the Applied Biosystems model 475 vapor phase protein sequence. PTH-amino acids were analyzed with an on-line microbore HPLC. Data were recovered and reduced with an Applied Biosystems 900-A data workstation and sequence-dedicated software. The sequence is compared to that of E. coli RNase HI in Table 2 and indicates some homology, especially in a 14 amino acid block starting at residue number 12 in the Thermus thermophilus RNase H enzyme. Table 2 is a comparison of these segments. In Table 2, exact matches are indicated by boldface, and conservative differences are underlined. The sequence data for E. coli RNase HI is from Kanaya and Crouch (1983) J. Biol. Chem. 258: 1276–1281.

TABLE 1

Amino acid composition of Thermus thermohilus RNase H

| Amino Acid | Abbrev. | Comp. by MW | # Residues T. thermophilus | # Residues E. coli |
|---|---|---|---|---|
| Aspartic acid + Asparagine | Asx | 13.863 | 14 | 14 |
| Glutamic acid + Glutamine | Glx | 21.715 | 22 | 20 |
| Serine | Ser | 4.820 | 5 | 4 |
| Glycine | Gly | 17.635 | 18 | 14 |
| Histidine | His | 6.273 | 6 | 5 |
| Arginine | Arg | 16.187 | 16 | 10 |
| Threonine | Thr | 7.887 | 8 | 10 |
| Alanine | Ala | 22.308 | 22 | 14 |
| Proline | Pro | 14.100 | 14 | 5 |
| Tyrosine | Tyr | 2.500 | 3 | 5 |
| Valine | Val | 7.382 | 7 | 9 |
| Methionine | Met | 3.254 | 3 | 4 |
| Cysteine | Cys | 3.622 | 4 | 3 |
| Isoleucine | Ile | 1.867 | 2 | 7 |
| Leucine | Leu | 19.596 | 20 | 12 |
| Phenylalaine | Phe | 6.965 | 7 | 2 |
| Lysine | Lys | 9.807 | 10 | 11 |

Calculated MW of sample: 20,018

TABLE 2

| N-terminal amino acid sequence of *Thermus thermophilus* RNase H. | | | | | | | | | | | | | | |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 |
| met | asn | pro | ser | pro | arg | lys | arg | val | ala | leu | phe | thr | asp | gly |
| met | | | | | leu | lys | gln | val | glu | ile | phe | thr | asp | gly |
| 16 | 17 | 18 | 19 | 20 | 21 | 22 | 23 | 24 | 25 | 26 | 27 | 28 | 29 | 30 |
| ala | cys | leu | gly | asn | pro | gly | pro | gly | gly | cys | ala | arg | leu | leu |
| ser | cys | leu | gly | asn | pro | gly | pro | gly | gly | tyr | gly | ala | ile | leu |
| 31 | 32 | 33 | 34 | | | | | | | | | | | |
| arg | phe | lys | ala ... | | *Thermus thermophilus* HB-8 | | | | | | | | | |
| arg | tyr | arg | gly ... | | *E. coli* | | | | | | | | | |

3. Heat stability comparison of *Thermus thermophilus* and *E. coli* RNases H

T. thermophilus and *E. coli* RNases H were preincubated in a reaction buffer minus poly-(rA) and oligo-(dT). The residual nuclease activities were determined after adding poly-(rA) and oligo-(dT).

10 units of *Thermus thermophilus* and *E. coli* RNases H were incubated for 10 minutes at 37° C., 45° C., 70° C., and 90° C. in 50 microliters of reaction buffer containing 0.01M Tris-HCl, pH 7.5, 10 mM $MgCl_2$; 0.1 mM EDTA, 1 mM dithiothreitol, and 0.1M NaCl. After readjusting the incubation temperatures back to 20° C. by incubation for 10 minutes in a 20° C. water bath, 50 microliters of 2 mM poly-(rA) and 0.2 mM oligo-(dT$_{18}$) in reaction buffer were added to the enzyme. After incubation for 45° C. for 20 minutes in the case of *T. thermophilus* RNase H and 37° C. for 20 minutes in the case of *E. coli* RNase H, the reactions were stopped and undigested poly-(rA) was precipitated by trichloroacetic acid precipitation. After centrifugation to pellet the undegraded poly-(rA), absorbance at 260 nm was determined for the supernatant solutions in order to determine the amount of poly-(rA) that had been digested. The absorbance values were corrected for background absorbance in a minus enzyme control and the values were normalized to the activity of *E. coli* RNase H and *Thermus thermophilus* RNase H which were not subjected to the heat treatment protocol. These values were set at 100% activity and the heat-treated activities are expressed as a percentage of these control values. The results (Table 3) indicate that *Thermus thermophilus* RNase H is stable upon heating, even up to 90° C. for 10 minutes, whereas the RNase HI from *E. coli* begins to lose activity at 45° C. for 10 minutes.

TABLE 3

Thermostability comparison of RNases H from *E. coli* and *Thermus thermophilus*

| Preincubation conditions | Residual Activity (%) | |
|---|---|---|
| | *E. coli* | *T. thermophilus* |
| 10 min., 37° C. | 100 | 100 |
| 10 min., 45° C. | 98 | 101 |
| 10 min., 70° C. | 8 | 98 |
| 10 min., 90° C. | 0 | 97 |

4. Screening for thermostable RNase H from other thermophilic organisms

Figure 4:
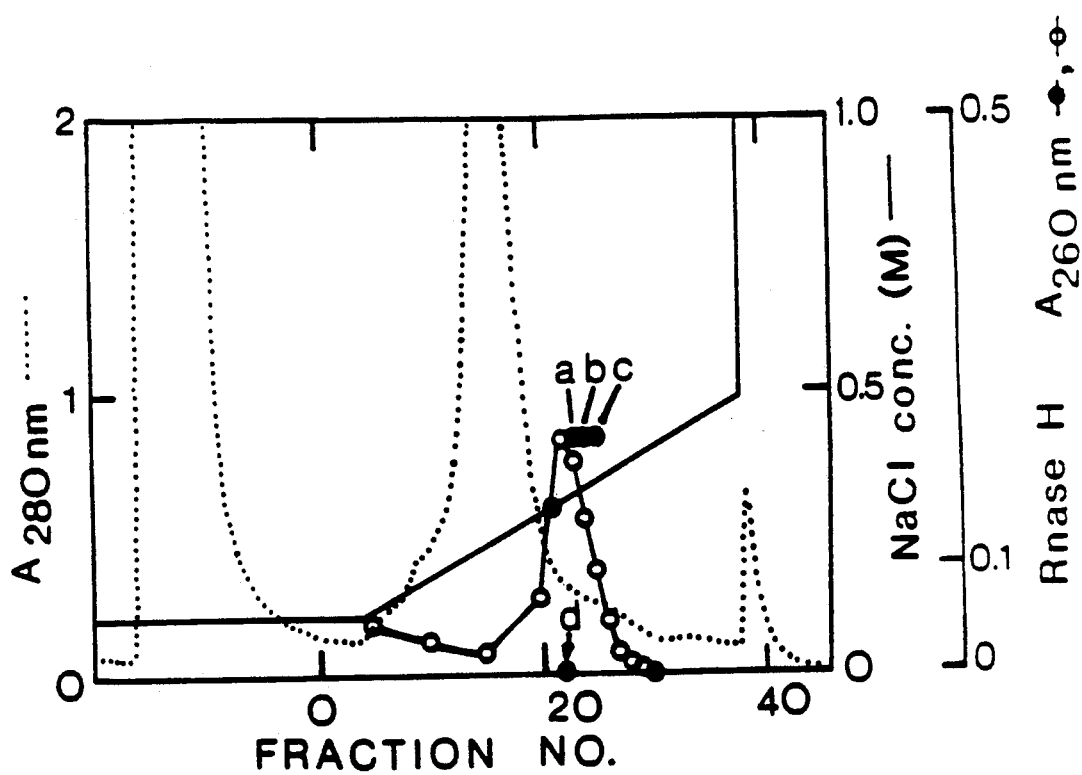
FIG. 4 is a chromatogram of *T. flavus* RNase H on BioRex 70.

A protein extract was prepared from the thermophilic organism *Thermus flavus* and was subjected to BioRex 70 column chromatography as described above. Fractions were assayed for RNase H activity. The elution profile is shown in FIG. 4. As with *Thermus thermophilus*, a single peak of RNase H activity was detected eluting at about 0.30M NaCl from the BioRex 70 column. The peak fraction was reassayed after preincubating aliquots of the peak fraction for 10 minutes at (A) 45° C., (B) 70° C. and (C) 90° C., as described in Table 3, and the residual RNase H activity was determined. At all pretreatment temperature conditions, the RNase H activity from *T. flavus* was stable and thus resembled the thermostable RNase H activity isolated from *Thermus thermophilus* HB8. The point labelled "D" in the graph is the RNase H activity when the assay was done in the absence of 100 μM oligo-(dT). The lack of poly-(A) digestion under these conditions confirms that this activity is indeed RNase H.

These experiments demonstrate that an analogous thermostable RNases H can be isolated from other thermophilic organisms. Organisms such as *Thermus aquaticus*, *Bacillus stereothermophilus* and bacteria isolated from deep-sea thermal vents (e.g. *Thermococcus litoralis*), using an approach similar to the isolation of RNase H from *Thermus thermophilus* may also be suitable for the isolation of thermostable RNase H.

We claim:

1. An essentially pure thermostable RNase H wherein the RNase H has a molecular weight of approximately 20,000 daltons and is capable of digesting added poly(rA) after incubation at 70° C. for 10 minutes and wherein the digestive capability after incubation at 70° C. for 10 minutes is at least about 98% of the digestive capability after incubation at 37° C. for 10 minutes.

2. The RNase H of claim 1 wherein the RNase H is isolated from *Thermus thermophilus*.

3. A process of digesting RNA in an RNA-containing molecule, wherein the RNA molecule is in duplex form with a DNA molecule, comprising exposing the nucleic acid duplex under conditions suitable for enzyme activity to an effective amount of an essentially pure preparation of a thermostable RNase such that the RNA is digested, wherein the RNase has a molecular weight of approximately 20,000 daltons and is capable of digesting added poly-(rA) after incubation at 70° C. for 10 minutes and wherein the digestive capability after incubation at 70° C. for 10 minutes is at least about 98% of the digestive capability after incubation at 37° C. for 10 minutes.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( D ) TOPOLOGY: linear (i i) MOLECULE TYPE: protein (v) FRAGMENT TYPE: N-terminal (v i) ORIGINAL SOURCE:
    (A) ORGANISM: Thermus thermophilus
    (B) STRAIN: HB-8

(x i) SEQUENCE DESCRIPTION: SEQ ID NO:1:

```
Met Asn Pro Ser Pro Arg Lys Arg Val Ala Leu Phe Thr Asp Gly Ala
 1               5                  10                    15

Cys Leu Gly Asn Pro Gly Pro Gly Gly Cys Ala Arg Leu Leu Arg Phe
              20              25                     30

Lys Ala
```

(2) INFORMATION FOR SEQ ID NO:2:

(i) SEQUENCE CHARACTERISTICS:
        (A) LENGTH: 30 amino acids
        (B) TYPE: amino acids
        (D) TOPOLOGY: linear (i i) MOLECULE TYPE: protein (v) FRAGMENT TYPE: N-terminal (v i) ORGINAL SOURCE:
        (A) ORGANISM: Escherichia coli (x) PUBLICATION INFORMATION:
        (A) AUTHORS: Ranaya, S.
        (C) JOURNAL: J. Biol. Chem.
        (D) VOLUME: 258
        (F) PAGES: 1276-1281
        (G) DATE: 1983

(x i) SEQUENCE DESCRIPTION: SEQ ID NO:2:

```
Met Leu Lys Gln Val Glu Ile Phe Thr Asp Gly Ser Cys Leu Gly Asn
 1               5                  10                    15

Pro Gly Pro Gly Gly Tyr Gly Ala Ile Leu Arg Tyr Arg Gly
              20              25
```